United States Patent [19]

Carlsson et al.

[11] 4,231,880

[45] Nov. 4, 1980

[54] ASSEMBLY FOR THE CLOSURE OF THE END OF A FLATTENED TUBE

[75] Inventors: Per-Olov A. V. Carlsson, Sösdala; Kaj O. Stenberg, Staffanstorp, both of Sweden

[73] Assignee: Gambro AB, Sweden

[21] Appl. No.: 961,517

[22] Filed: Nov. 17, 1978

[30] Foreign Application Priority Data

Nov. 18, 1977 [SE] Sweden ............................. 7713020

[51] Int. Cl.³ ............................................. B01D 13/00
[52] U.S. Cl. ............................ 210/321 B; 210/494 M; 210/497.1
[58] Field of Search .......... 210/321 B, 321 A, 321 R, 210/494 M; 160/385, 386, 391–395, 397–398; 422/48

[56] References Cited

U.S. PATENT DOCUMENTS

| Re. 27,510 | 10/1972 | Hoeltzenbein | 210/321 A |
|---|---|---|---|
| 3,709,367 | 1/1973 | Martinez | 210/321 B |
| 3,712,474 | 4/1970 | Martinez | 210/321 A |
| 3,743,098 | 7/1973 | Martinez | 210/321 B |
| 3,880,760 | 4/1975 | Flandoli | 210/321 B |
| 3,962,095 | 6/1976 | Luppi | 210/321 B |
| 3,963,621 | 6/1976 | Newman | 210/321 B |
| 3,977,976 | 8/1976 | Spaan et al. | 210/321 B |
| 3,986,961 | 10/1976 | Martinez | 210/321 B |
| 4,008,157 | 2/1977 | Miller et al. | 210/321 B |
| 4,028,253 | 6/1977 | Miller et al. | 210/321 B |
| 4,059,530 | 11/1977 | Luppi | 210/321 B |

FOREIGN PATENT DOCUMENTS

1417446 12/1975 United Kingdom .
1433512 4/1976 United Kingdom .
1435938 5/1976 United Kingdom .

*Primary Examiner*—Robert H. Spitzer
*Assistant Examiner*—E. Rollins Cross
*Attorney, Agent, or Firm*—Lerner, David, Littenberg & Samuel

[57] ABSTRACT

Assembly is disclosed for clamping and sealing the end of a flattened tube. The assembly includes a groove for receiving an end of a flattened tube, and a clamping member including a beaded portion for clamping and sealing the end of a flattened tube when the clamping member is in a clamping position within the groove and the end of the flattened tube is properly disposed in said groove. The groove has a first groove surface and a second surface disposed at an oblique angle relative to said first surface, the second surface including a clamping portion, and the clamping member including a locking portion adapted to mate with said clamping portion of the second surface of the groove when the clamping member is in the clamping position within the groove, whereby the beaded portion is held in its sealing position relative to the end of the flattened tube disposed within the groove.

10 Claims, 4 Drawing Figures

ASSEMBLY FOR THE CLOSURE OF THE END OF A FLATTENED TUBE

BACKGROUND OF THE INVENTION

The present invention relates to an apparatus for clamping a flattened tube in a diffusion device. More particularly, the present invention relates to an apparatus for sealing a semi-permeable membrane in a dialysis device.

A number of apparatuses for closing tubular membranes are known. For example, U.S. Pat. No. Re 27,510 discloses a device in which the ends of a tubular membrane are folded around a highly elastic terminal tube 9 and pulled together under strong friction so as to be leak-proof. The patentee thus employs a conical bore 8 of a confining rim 10 in the outer casing 13 as best shown in FIG. 4 of the patent.

U.S. Pat. No. 3,712,474 teaches another such device which includes connector units 52 and 54 as best shown by FIG. 6 of the patent. In each unit, patentee includes a substantially resilient body portion 60 in a relatively less flexible cup element 62. By closely conforming the internal cup dimension to that of the body and by forming the body of a substantially resilient material, a snug fit is provided. Moreover, at least one O-ring 72 supported by the body insures a better fluid tight seal and prevents a possibility that the membrane will pull loose. Similar teachings are contained in U.S. Pat. Nos. 3,709,367 and 3,743,098.

U.S. Pat. No. 3,880,760 discloses yet another such device which includes a core cover section 2 adapted to mate with a core base section 1 with the ends of the tubular membrane therebetween. A similar structure is employed at the other end of the tubular membrane as shown by FIG. 2 of the patent. The core cover and core base sections are provided with seals 5 and 6 to seal the membrane tube 9 with the open end 7 of the blood inlet conduit within the membrane tube.

In a similar vein is U.S. Pat. No. 3,962,095 which discloses blood inlet and outlet means 26 for connection with arterial and veinous lines attached to a casing 22. The cover plates 28 are secured to the casing by means of screws 30. The cover plate 28 and the casing 22 carry seals 32 to seal the free ends of the membrane tube 12 with the blood inlet and blood outlet means 26.

U.S. Pat. No. 4,059,530 discloses blood inlet and outlet ports in a dialyzer membrane tube 3 comprising a connector 30 connected to a header 32 through a hole in the membrane. The header 32 is thus located internally in the tubular membrane. A locking disc 33 locks the membrane tube 3 against one wall of the header 32. The header is provided with internal chambers 35 communicating with the interior of the tubular membrane 3. The end of the tube is shown squeezed between connector 30 and a wall opposite the connector.

Other similar devices are shown in U.S. Pat. No. 3,963,621, British Pat. No. 1,417,446 and British Pat. No. 1,433,512. U.S. Pat. No. 3,963,621 merely states that a tube 18 communicates conventionally with the end 20 of a membrane 16. FIG. 3 of British Pat. No. 1,433,512 shows a membrane tube 2 pleated around a rigid connecting plug 38. Medical plaster 41 is applied around the membrane tube and the tube is secured by means of two knotted cords 42 and 43 in the annular grooves 39 and 40. British Pat. No. 1,417,446 merely discloses that the core 1 includes an opening in which a sleeve 31 fits so that the blood tube 12 can be connected to the membrane tube 2.

SUMMARY OF THE INVENTION

In accordance with the present invention, an assembly has now been prepared including a groove for receiving an end of a flattened tube and a clamping member including a beaded portion for clamping and sealing the end of a flattened tube when said clamping member is in a clamping position within said groove and the end of the flattened tube is properly disposed in said groove, said groove comprising a first groove surface and a second groove surface disposed at an oblique angle relative to said first groove surface, said second groove surface including a clamping portion, and said clamping member including a locking portion adapted to mate with said clamping portion of said second groove surface when said clamping member is in its said clamping position within said groove whereby said beaded portion is held in its sealing position relative to the end of a flattened tube properly disposed within said groove. The first and second groove surfaces are preferably planar.

In a preferred embodiment of the present invention, the clamping member is in the form of a clamping strip including a clamping rail fitting into the groove, said clamping rail having a first clamping surface including the beaded portion on its face and a second clamping surface, said beaded portion on said first clamping surface cooperating with the first groove surface and the second clamping surface cooperating with the second groove surface so as to hold said end of said flattened tube in a fluid tight seal between the first groove surface and the beaded portion on said first clamping surface. Such an apparatus has been found to be advantageous because of its simple design and very secure sealing of the end of a tube.

In another preferred embodiment of the present invention, the groove is defined in the wall of a cylindrical core or bobbin around which the tube is helically wound. The groove is preferably arranged axially on the surface of the bobbin. The end of the tube is disposed in the groove and the clamping member is arranged so that the outer surface of the clamping member coincides with the outer surface of the bobbin to complete a cylindrical shape. The clamping member can be manufactured separately and thus be detachable from the bobbin. Such an arrangement is advantageous because it provides simple design and secure sealing, while allowing good flow conditions inside the tube due to the smooth cylindrical surface formed by the clamping member and bobbin.

In another preferred embodiment, the outer surface of the above-mentioned clamping strip defines a plurality of peripherally extending surfaces which are separated by grooves. Also, the second clamping surface of the clamping strip preferably defines a series of substantially radially extending protuberances separated by grooves. Such a design allows the clamping strip to be bendable and also allows the use of less material in preparing the clamping strip. Thus, such a design insures that the beaded portion can be reliably pressed against the flattened tube along the whole of its opening.

In yet another preferred embodiment of the present invention, the clamping portion on the second groove surface consists of a bead along the upper end of the second groove surface. The bead preferably extends inwardly into said groove. Such a bead in combination with the obliquely positioned second surface of the groove allows a pressure on the beaded portion on the first clamping surface of the clamping member which can be adapted so as to achieve an effective compressing and sealing of the tube against the first groove surface.

In still another preferred embodiment of the present invention, the above-mentioned bead along the upper end of the second groove surface is arranged to cooperate with a chamber or recess in the outer surface of the clamping member at the transition between said outer surface and the clamping rail. The cooperation of the bead and the recess and the construction as a whole of the clamping assembly allows the end of a flattened tube to be brought into position in the groove and pressed together without substantial stretching or displacement of the material of the tube, which stretching or displacement may otherwise cause breakage or leakage in the tube.

The assembly of the present invention may be used in any suitable dialysis arrangement or a so-called artificial kidney of the type disclosed in U.S. Application No. 902,353 filed May 3, 1978, the disclosure of which is incorporated herein by reference. While the assembly of the present invention is intended primarily to be used in connection with dialysis, it will, however, be clear to those skilled in this art that the assembly may be used for many other diffusion and/or filtration processes such as use in oxygenators. Thus, the term "fluid" herein is intended to cover gases as well as liquids.

BRIEF DESCRIPTION OF THE DRAWINGS

The present invention may be better understood with reference to the Figures, which are described as follows.

DETAILED DESCRIPTION

The present invention may be described in greater detail with reference to the figures shown in the preferred embodiments of the present invention, in which like numerals refer to like portions thereof.

Figure 1:
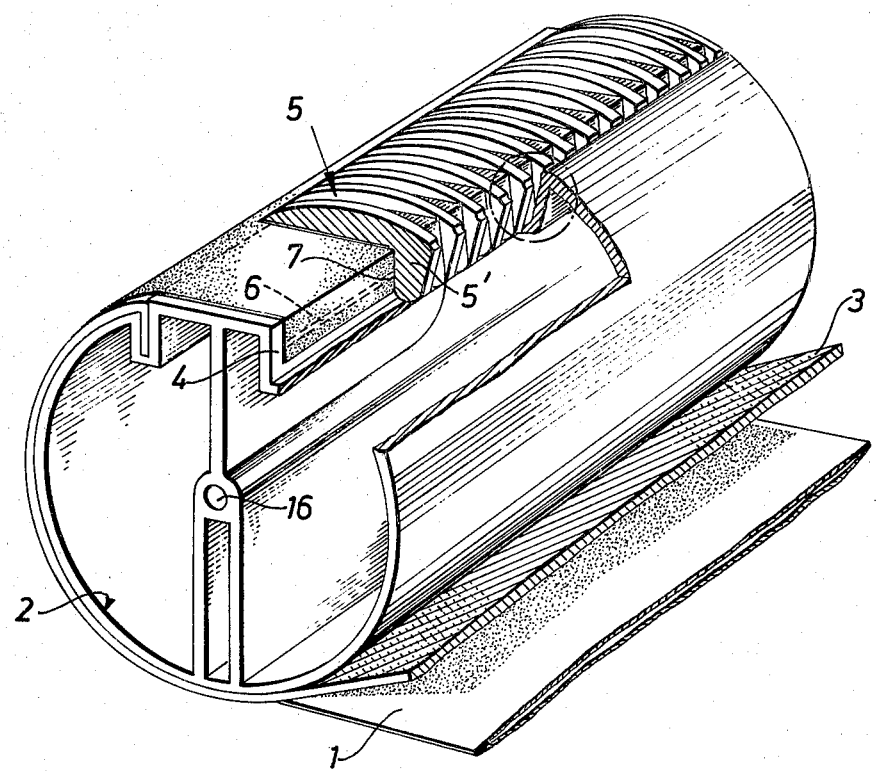
FIG. 1 is a perspective view of an assembly in accordance with the present invention partially broken away to show the clamping rail in the groove.

Referring specifically to FIG. 1, a flattened tube 1 is wound around a core or bobbin 2 together with a supporting net 3. The inner end of the tube 1 is secured in a groove 4 by a clamping strip 5. A fluid tight seal of the end of tube 1 is achieved along the line 6 by a clamping bead 7 on a leg or rail 5' of the clamping strip 5. A feed duct 16 supplies a liquid for the interior of the tube 1. The introduction of this liquid into the tube may occur in any suitable manner, for example, by the apparatus shown in U.S. Patent Application No. 902,353 filed May 3, 1978, the disclosure of which is incorporated herein by reference.

Figure 1A:
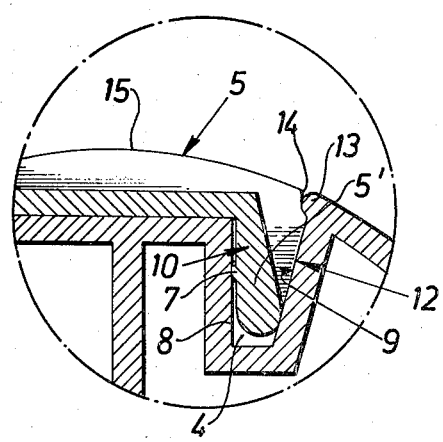
FIG. 1a is a transverse cross-sectional view of a portion of the assembly shown in FIG. 1.

Referring to FIG. 1a, the operation of the apparatus of the present invention is shown, but for sake of clarity, the flattened tube has been left out. The groove 4 consists of a first groove surface 8 which in the embodiment shown has been given a plane shape and a second groove surface 9 which is in an oblique position in relation to the first groove surface 8. The clamping leg or rail 5' of the clamping strip 5 consists of a first clamping surface 10 provided with a clamping bead 7 and of a second clamping surface 12 which is intended to cooperate with the oblique groove surface 9. The oblique groove surface 9 terminates at the top of the groove in a clamping bead 13 which is adapted so as to cooperate with a recess 14 in the clamping strip 5 at the transition between the peripheral surface 15 of the clamping strip and the second clamping surface 12. By the construction shown, a pressure is directed substantially perpendicularly to the tube along the line 6 on the groove surface 8.

Figure 2:
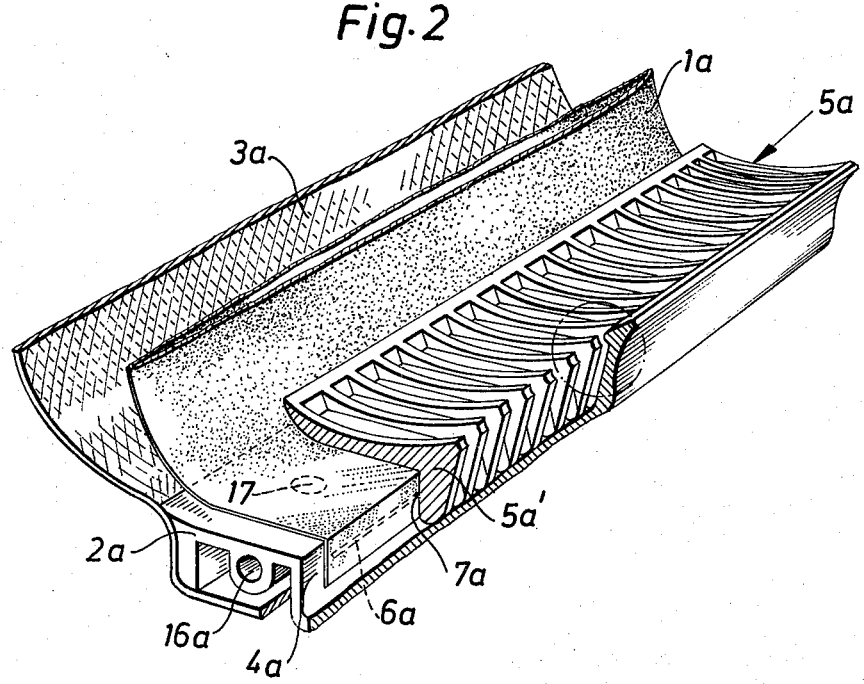
FIG. 2 is a perspective view of another embodiment of the assembly of the present invention partially broken away to show the clamping rail in the groove.
Figure 2A:
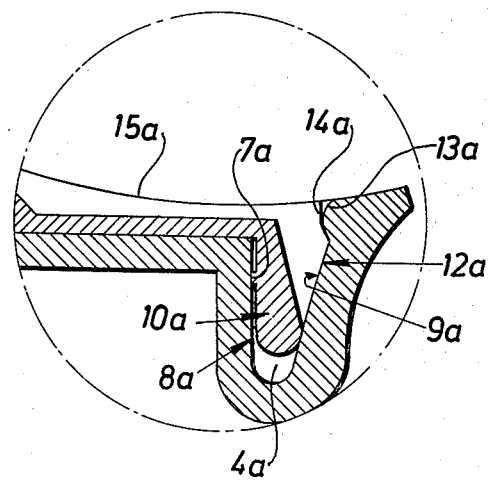
FIG. 2a is a cross-sectional view of a portion of the clamping assembly shown in FIG. 2.

Referring to FIG. 2, a construction of an apparatus in accordance with the present invention is shown which in principle is the same as that shown in the embodiment in FIG. 1 with regard to the actual sealing of the tube 1. Accordingly, corresponding parts have been given the same reference designation but with the addition of the letter a. Thus, the tube 1a is sealed by means of a clamping strip 5a along the line 6a by a clamping bead 7a on the clamping leg or rail 5a'. Thus, in this embodiment of the invention, the clamping leg or rail 5a' is fitted into a groove 4a arranged in a coupling strip 2a which coupling strip corresponds to the drum or bobbin 2 in FIG. 1. For a more detailed discussion of the structure of a suitable coupling strip, reference is made to U.S. Patent Application No. 902,353 filed May 3, 1978. The groove 4a is formed by a first groove surface 8a and a second groove surface 9a arranged in an oblique position in relation to the first groove surface 8a. The clamping bead 7a on the first clamping surface 10a cooperates with the first groove surface 8a and the clamping surface 12a cooperates with the groove surface 9a so as to seal the tube between said clamping bead 7a and said groove surface 8a. The clamping bead or rail 5a is held securely in position by a clamping bead 13a on the upper portion of the second groove surface 9a and a recess 14a in the clamping strip 5a at the transition between the peripheral surface 15a of the clamping strip and the clamping surface 12a. Thus, liquid can be withdrawn from the space inside the tube via a duct 16a connected to the tube 1 at the opening 17 in a manner described, for example, in U.S. Patent Application No. 902,353 filed May 3, 1978 mentioned above. Other types of connections known in the art may, of course, also be used.

It will be understood that the embodiments described above are merely exemplary and that persons skilled in the art may make many variations and modifications without departing from the spirit and scope of the invention. For example, the form and shape of the individual parts included in the apparatus of the present invention may be varied considerably without thereby exceeding the scope of the invention. All such modifications and variations are intended to be included within the scope of the invention as defined by the appended claims.

What is claimed is:

1. A clamping assembly for clamping and sealing the end of a flattened tube, comprising a groove for receiving an end of a flattened tube, and a clamping member including a beaded portion for clamping and sealing the end of a flattened tube when said clamping member is in a clamping position within said groove and the end of the flattened tube is properly disposed in said groove, said groove comprising a first groove surface and a second groove surface disposed at an oblique angle relative to said first groove surface, said second groove surface including a clamping portion, and said clamping member including a locking portion adapted to mate with said clamping portion of said second groove surface when said clamping member is in its said clamping position within said groove whereby said beaded portion is held in its sealing position relative to the end of a flattened tube properly disposed within said groove.

2. A clamping assembly according to claim 1 in which said clamping member includes a clamping rail fitting into said groove, said clamping rail having a first clamping surface and a second clamping surface, said first clamping surface including said beaded portion, said beaded portion on said first clamping surface cooperating with said first groove surface and said second clamping surface cooperating with second groove surface so as to hold said end of said flattened tube in a fluid tight seal between said first groove surface and said beaded portion on said first clamping surface.

3. A clamping assembly according to claim 1 or 2 in which said groove is defined in a wall member, said wall member and the outer surface of said clamping member defining a substantially cylindrical shape when said clamping member is in a clamping position within said groove.

4. A clamping assembly according to claim 3 in which said flattened tube is wound helically around the cylinder.

5. A clamping assembly according to claim 1 or 2 in which said first groove surface is substantially planar.

6. A clamping assembly according to claim 1 or 2 in which said second groove surface is substantially planar.

7. A clamping assembly according to claim 1 in which the outer surface of said clamping member defines a plurality of peripherally extending surfaces separated by grooves.

8. A clamping assembly according to claim 2 in which said second clamping surface defines a series of protuberances separated by grooves.

9. A clamping assembly according to claim 1 or 2 in which said clamping portion consists of a bead along the upper end of said second groove surface.

10. A clamping assembly according to claim 2 in which a recess in said clamping member at the transition between the outer surface of the clamping member and said second clamping surface cooperates with said clamping portion to secure the clamping member into said groove.

* * * * *